United States Patent
Boss et al.

(10) Patent No.: US 6,776,962 B1
(45) Date of Patent: Aug. 17, 2004

(54) INTEGRATED OPTICAL WAVEGUIDE SENSOR

(75) Inventors: Pamela A. Boss, San Diego, CA (US); Stephen H. Lieberman, La Mesa, CA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 17 days.

(21) Appl. No.: 10/097,765

(22) Filed: Mar. 13, 2002

Related U.S. Application Data

(63) Continuation-in-part of application No. 09/593,675, filed on Jun. 14, 2000.

(51) Int. Cl.[7] .............................................. G01N 21/65
(52) U.S. Cl. ..................................... 422/82.11; 356/301
(58) Field of Search .......................... 422/82.05, 82.09, 422/82.11; 436/164, 171; 356/301

(56) References Cited

U.S. PATENT DOCUMENTS

| | | | | |
|---|---|---|---|---|
| 5,082,629 A | * | 1/1992 | Burgess et al. | 422/82.11 |
| 5,266,498 A | * | 11/1993 | Tarcha et al. | 436/525 |
| 5,527,712 A | * | 6/1996 | Sheehy | 436/525 |
| 5,814,516 A | * | 9/1998 | Vo-Dinh | 435/287.2 |
| 2002/0128234 A1 | * | 9/2002 | Hubbel et al. | 514/100 |

OTHER PUBLICATIONS

Heyns, J.B et al, "SERS Study of the Interaction of Alkali Metal Ions with a Thiol–Derivatized Dibenzo–18–Crown–6" Anal. Chem., vol. 66, 1572–1574, 1994.*

Boss, P. A., etal.; Detection of Nitrate and Sulfate Anions by Normal Raman Sprectroscopy and SERS of Cationic–Coated, Silver Substrates; Applied Spectroscopy pp 1126–1135; vol. 54 Nr. 8, 2000; U.S.A.

Xu, Wenbo, et at.; Evanescent Wave Surface Enhanced Raman Scattering from Organic Molecules Bonded to "Optimal Chemical Benches"; Opt. Soc. American Technical Digest pp. 378–381; vol . 21, 1995, U.S.A.

* cited by examiner

*Primary Examiner*—Jeffrey R. Snay
(74) *Attorney, Agent, or Firm*—Celia C. Dunham; Michael A. Kagan; Peter A. Lipovsky

(57) ABSTRACT

An integrated optical waveguide sensor system includes: an optical waveguide having a monolithic and roughened metallic layer on which a self-assembled monolayer is formed; an optical energy source for generating an optical excitation signal; and a spectrometer for detecting spectra of optical energy emitted from the optical waveguide. The waveguide facilitates multiple SERS responses resulting from interactions between the optical excitation signal and an analyte of interest that may be present on the surface of the self-assembled monolayer. Thus, the sensor system provides a sensor for detecting organic contaminants with a sensitivity of ppm and even ppb in some cases.

15 Claims, 7 Drawing Sheets

INTEGRATED OPTICAL WAVEGUIDE SENSOR

CROSS-REFERENCE TO RELATED APPLICATIONS

This is a continuation-in-part of application Ser. No. 09/593,675, filed 14 Jun. 2000, entitled A Metal And Glass Structure For Use in Surface Enhanced Raman Spectroscopy and Method for Fabricating Same (Navy Case No. 79987).

BACKGROUND OF THE INVENTION

The present invention generally relates to a sensor for detecting anionic nutrients, and more particularly to a sensor that employs surface enhanced Raman spectroscopy (SERS) for detecting very small concentrations of anions including toxic anions such as perchlorate, chromate, dichromate, and cyanide.

Detection and control of ionic pollutants (i.e., nitrates, sulfates, and phosphates) are important for the protection of the environment. When waste waters that contain ionic nutrients are discharged into surface waters, they can promote the unnatural growth of blue-green algae to the detriment of other plant and animal life. The decay of dead algae causes a reduction in the amount of dissolved oxygen available in the water. Eventually, the excess concentration of nutrients in the body of water results in the inability of the body to support any other life forms, a process called eutrophication. Besides eutrophication, ionic pollutants have been blamed for the increased incidences of red tide, blooms of toxic, single-celled organisms, such as dinoflagellates, that have caused die-offs of fish, dolphins, manatees, and other aquatic animals. Dinoflagellates are thought to be responsible for the human disease ciguatera. Symptoms of this disease include loss of coordination, slowed heartbeat, and diarrhea. Most people recover, but some victims die. Dinoflagellates are also blamed for paralytic shellfish poisoning.

Nitrates represents a potential human health hazard, and nitrate contamination is the most common reason for the shutdown of public water supply wells. When consumed, nitrates are converted to N-nitroso compounds in the human stomach. Some of these compounds are carcinogenic. It has been suggested that stomach cancer is associated with nitrate uptake. Furthermore, certain species of bacteria in humans can enzymatically reduce nitrate to nitrite. The toxic effects of nitrites include vasodilation, lowered blood pressure, and formation of methemoglobin, a non-oxygen carrying form of hemoglobin. In infants, methemoglobinemia is known as "blue baby syndrome."

While ionic pollutants can enter the water supply by a number of natural means, the most significant contributions result from man made processes, such as fertilizers used in agriculture and effluents from sewage treatment plants. In order to protect the public health, a need exists for a sensor capable of monitoring ionic pollutants continuously, simultaneously, in real time, insitu, and with little or no sample preparation. Such a sensor needs to be able to differentiate ionic species, not suffer from interferences, be able to detect ppm concentrations of pollutants, and be reversible. Technologies which have been used in the past include colorimetry, UV-VIS absorption spectrometry, Raman spectrometry, electrochemical methods such as amperometry, or potentiometry using ion selective electrodes, and ion exchange chromatography. However, these approaches do not meet all the desired criteria of specificity, sensitivity, reversibility, real-time, etc.

In the 1970s, it was discovered that Raman scattering from molecules of an analyte of interest adsorbed on noble metals such as silver, copper, and gold when irradiated with optical energy can be enhanced by as much as $10^6$ to $10^7$ compared to merely irradiating the analyte.

This phenomenon is known as surface enhanced Raman spectroscopy (SERS). A SERS structure generally includes a silver, gold, or copper metal layer formed on a substrate and is used to detect the presence of an analyte by examining the emissions from the substrate when irradiated with optical excitation energy. SERS emissions, or spectra, have been used to detect and identify trace organic materials and as a detection method in gas chromatography, liquid chromatography, and thin layer chromatography. Electrochemical SERS and SERS of chemically modified surfaces have been used to detect aromatic compounds, chlorinated hydrocarbons, and other organic contaminants of environmental concern in the ppm range.

Therefore, a need exists for a robust sensor that can detect and identify trace amounts of anionic nutrients and which can overcome the aforementioned problems.

SUMMARY OF THE INVENTION

The present invention is directed to an integrated optical waveguide sensor system for detecting contaminants with a sensitivity of ppm and even ppb in some cases. The sensor includes: an optical waveguide having a monolithic and roughened metallic layer on which a self-assembled monolayer is formed; an optical energy source for generating an optical excitation signal to be coupled into the waveguide; and a spectrometer for detecting spectra of optical energy emitted from the optical waveguide. The waveguide facilitates multiple SERS responses resulting from interactions between the optical excitation signal and an analyte of interest that may be present on the surface of the self-assembled monolayer. Certain of the emitted spectra from the waveguide may be correlated to the presence of specific analytes in contact with the self-assembled monolayer.

These and other advantages of the invention will become more apparent upon review of the accompanying drawings and specification, including the claims.

BRIEF DESCRIPTION OF THE DRAWINGS

Throughout the several views, like elements are referenced using like references.

DESCRIPTION OF THE PREFERRED EMBODIMENT

The present invention is described with reference to FIG. 1 where there is shown an integrated optical waveguide sensor 200 for detecting anions using surface enhanced Raman spectroscopy (SERS). By way of example, the invention may be used to detect nitrate ions for assessing the quality of drinking water. The invention also may be used to monitor concentrations of nitrates and phosphates to minimize run-off of fertilizers into aquatic bodies such as a ponds, lakes, or rivers. Other applications of the invention include monitoring the concentration of ionic nutrients in the effluent of sewage treatment plants to minimize the release of such nutrients into the environment, and thereby better manage aquatic ecosystems.

Figure 1:
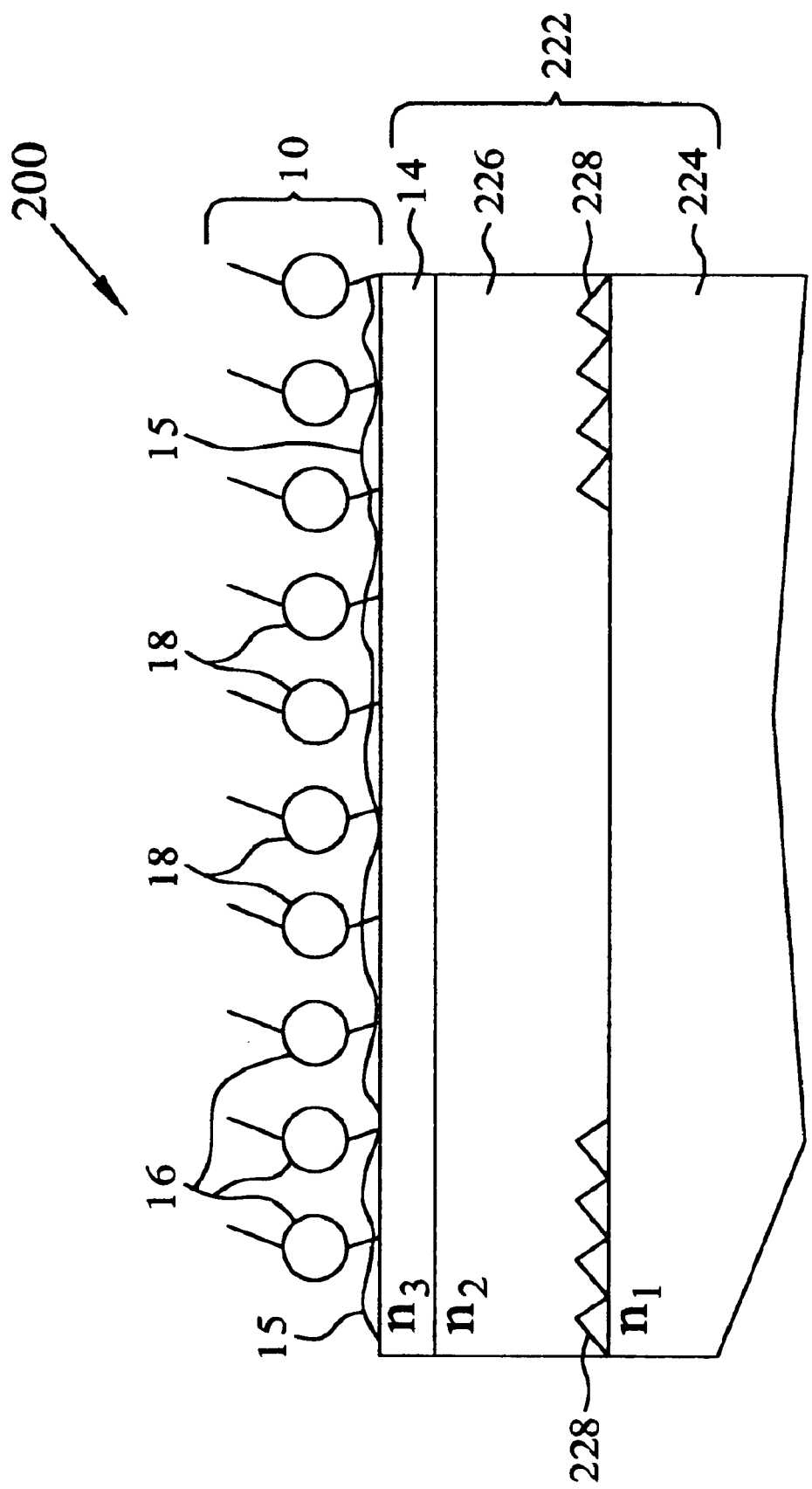
FIG. 1 is a cross-sectional view of an integrated optical waveguide sensor that embodies several features of the present invention.
Figure 2:
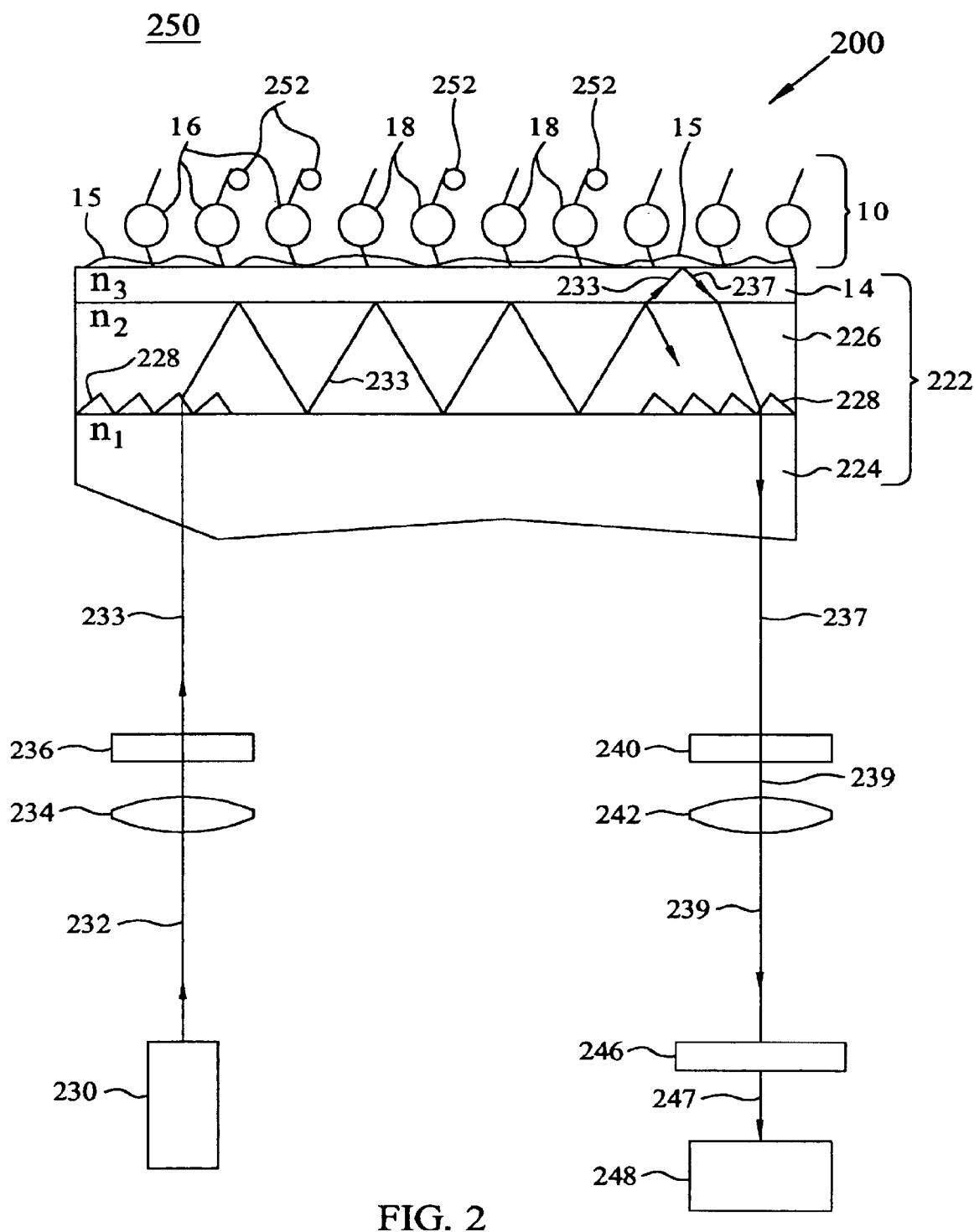
FIG. 2 shows the application of the integrated optical waveguide sensor of FIG. 1.
Figure 3:
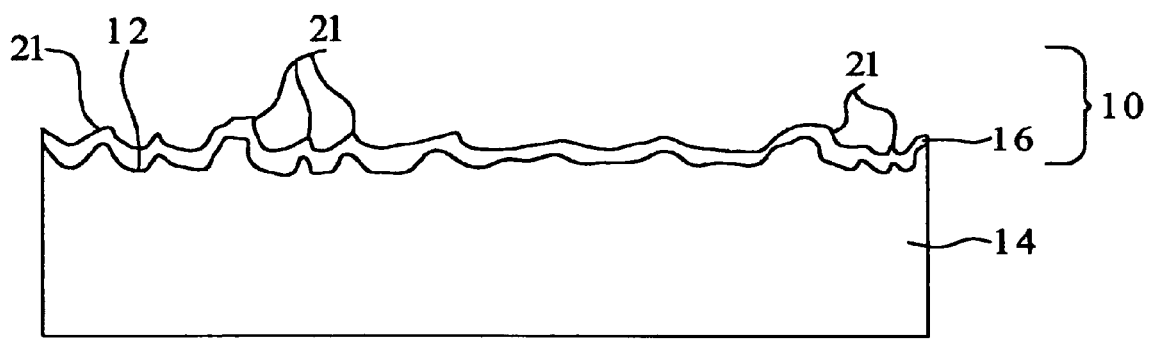
FIG. 3 is a cross-sectional view of a SERS structure embodying various features of the present invention.
Figure 4:
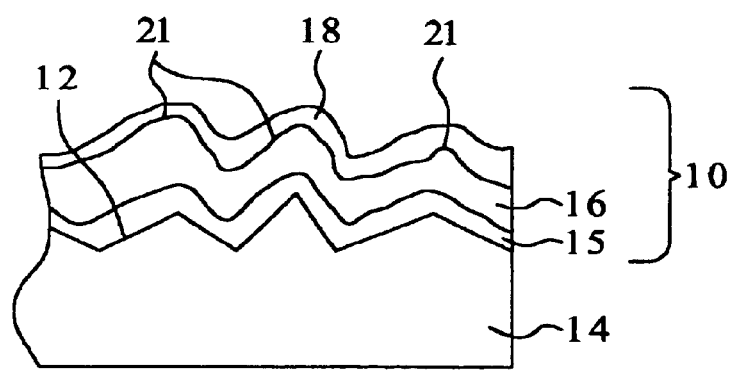
FIG. 4 is an enlarged view of a section of the structure depicted in FIG. 2.

Referring to FIG. 1, integrated optical waveguide sensor 200 includes a SERS structure 10 affixed to an optical assembly 222. Optical assembly 222 is a layered structure that includes a optical element 14 bonded to a transparent optical element 226 which in turn is bonded to a optical element 224. Optical assembly 222 also includes spaced apart optical coupling gratings 228 affixed between elements 226 and 224. In the scope of the invention, any or all of optical elements 224, 226, and 14 may be implemented as translucent or transparent structures, or even be implemented as having some combination of both translucent and transparent regions. Optical element 224, optical element 226, and optical element 14, may each be made of glass and have indices of refraction $n_1$, and $N_2$, and $n_3$ respectively, where $n_2 \rangle n_1$, and $n_2 \rangle n_3$. Optical assembly 222 is commercially available from WZW-Optic of Balgach, Switzerland Referring to FIGS. 1 and 2, when in contact with an analyte of interest and illuminated with appropriate excitation energy, SERS structure 10 produces optical emissions having unique characteristics that are used to detect the presence of an analyte of interest 252 in an aquatic or gaseous environment 250. By way of example, analytes may include organic, metallic, and anionic contaminants. Referring to FIGS. 3 and 4, SERS structure 10 includes a specially roughened surface 12 formed on optical element 14 which may be made of optically translucent or transparent materials such as glass or hafnium oxide, on which an adhesion layer 15 is formed. Adhesion layer 15 promotes the bonding of the metal layer 16 to optical element 14. The metal layer 16 is formed, as for example, by vapor deposition, onto adhesion layer 15 to create a monolithic and roughened, patterned metal layer as shown in FIG. 4. A thiol coating, or self-assembled monolayer 18 on metal layer 16 protects metal layer 16 from chemical contamination, thereby extending the lifetime of SERS structure 10 when exposed to aqueous environments from minutes or hours to months. The roughened surface 12 facilitates both a good SERS response and adhesion of the metal layer 16 to the optical element 14.

In the fabrication of structure 10, optically transparent optical element 14, such as a clear borosilicate glass, is carefully cleaned and prepared prior to having a metal film deposited on it. First, optical element is immersed in a heated or boiling liquid reagent or reagents to remove any oils, metallic materials, and other contaminants that may be present on optical element 14. By way of example, optical element 14 may be immersed in a Pyrex beaker containing boiling nitric acid for about 30 minutes. However, other liquid reagents also may be used such as hydrofluoric acid, hydrochloric acid, potassium hydroxide. Next, optical element 14 is removed from the boiling nitric acid and rinsed in either deionized or distilled water. After the water rinse, optical element 14 is immersed in hot or boiling methanol for about 30 minutes, followed by immersion in boiling acetone for about 30 minutes. This procedure removes any remaining organic contaminants. Optical element 14 then is removed from the methanol and allowed to air dry, as for example, about 1 hour.

Referring to FIG. 3, cleaned surface 12 of optical element 14 is etched to provide surface 12 with a surface roughness having a maximum peak to valley depth of about 16,000 Å, an average peak to valley depth of about 2,500 Å, and a peak to peak periodicity of about 12.5 microns. The roughness of surface 12 and its periodicity were measured using a Dektak$^3$ST Surface Profiler (Vecco Sloan Technology). In contrast, commercial white glass generally has a surface having a peak to valley depth of about 200,000 Å, an average peak to valley depth of about 43,700 Å, and a peak to peak periodicity of about 100 microns. The combination of surface roughness and peak to peak periodicity of surface 12 provides SERS structure 10 with a greatly enhanced SERS response compared to that of SERS structures that include commercial glass. In one implementation of the invention, portions of or selected regions of surface 12 may be etched using a chemical etchant such as an HF based cream such as Velvet Etching Cream, manufactured by McKay International. Experience has shown that etching white glass for approximately 1 minute provides the surface roughness characteristics described above. Alternatively, surface 12 may be roughened using standard photo lithographic techniques.

Figure 5:
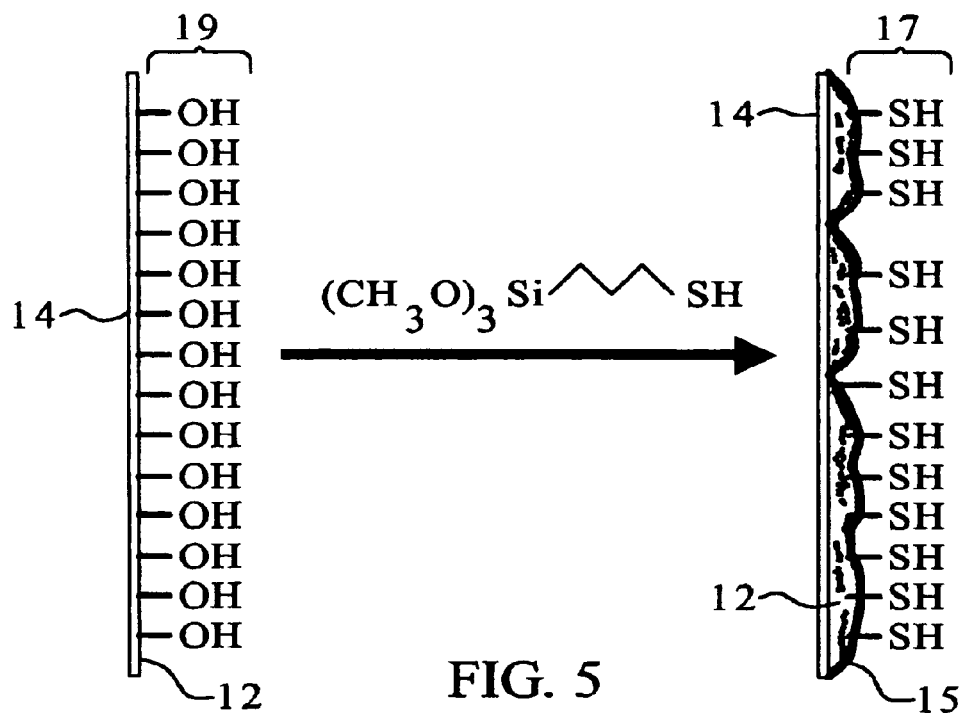
FIG. 5 represents the formation of a silane layer on surface of a glass substrate in the manufacture of the invention.
Figure 6:
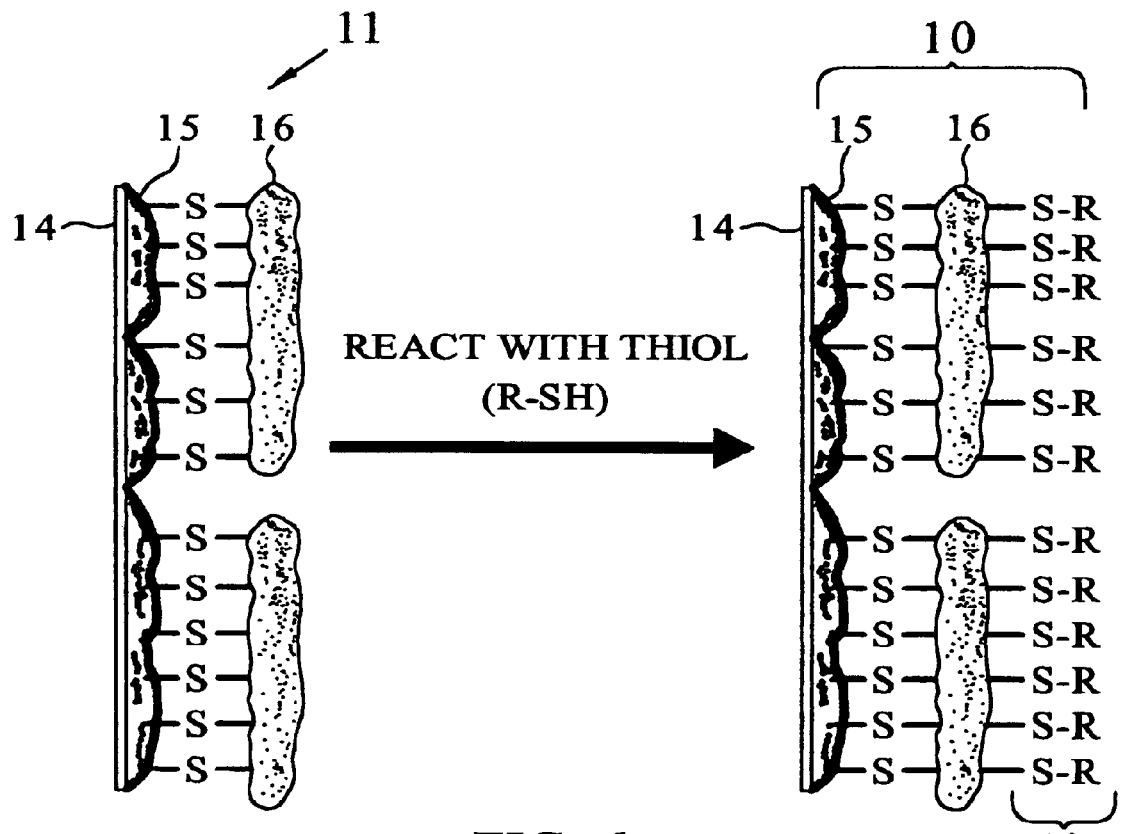
FIG. 6 shows the formation of a self-assembled monolayer (SAM) layer on the metal islands bonded to the glass substrate in the manufacture of the SERS structure of FIGS. 1 and 2.

After etching, optical element 14 is rinsed with distilled or deionized water, followed by an ethanol rinse. The cleaned, etched optical element 14 then is derivitized in a silanization agent such as a 1:10 mixture by volume of (3-mercaptopropyl) trimethoxysilane (MCTMS) in ethanol for about 24 hours to form adhesion layer 15 on roughened surface 12, shown in FIG. 4. Referring now to FIG. 5, it is believed that the derivitization process causes a silane layer 17 to bond to ⁻OH functional groups 19 believed to be present on surface 12 in applications wherein optical element 14 is made of transparent glass or hafniun oxide (hafilia) substrate. Optical element 14 was next rinsed in ethanol to remove unreacted (3-mercaptopropyl) trimethoxysilane and allowed to air dry. As illustrated in FIG. 6, adhesion layer 15 promotes bonding between roughened surface 12 and monolithic, roughened metal layer 16 having metal peaks 21.

Still referring to FIG. 4, and by way of example, a metal such as gold, silver, or copper may be vapor deposited onto adhesion layer 15 to form monolithic and roughened metal layer 16 that generally has the contours of roughened surface 12. In one implementation of the invention, a gold layer was vapor deposited onto roughened surface 12 using material evaporated from an Adrich, 99.99% pure gold wire using a Vecco Model EC 200 vapor deposition system. As a result of the aforesaid processing, adhesion layer 15 durably bonds metal layer 16 to roughened surface 12 so that SERS structure 10 may provide an effective SERS response after being immersed in an aqueous environment for months.

After depositing metal layer 16 onto adhesion layer 15 a patterned structure 11, as shown in FIG. 6, is created.

Patterned structure 11 may be placed in a dilute ethanolic thiol solution at ambient temperature and pressure for a period of time, such as 24 hours. While structure 11 is immersed in the thiol solution, metal layer 16 reacts with the thiol to form a durable, self-assembled monolayer 18 on the metal layer 16, as shown in FIG. 6. Thiols selected for fabricating self-assembled monolayer 18 may be selected which have an affinity for the analyte (organic compounds, metal ions, or anions) of interest. Moreover, detection limits in the ppb to ppm range are possible. TABLE 1 provides, by way of example, a list of examples of thiols and analytes that may be detected using such thiol coatings. However, TABLE 1 is not to be considered exhaustive.

TABLE 1

| Thiol Type | Useful For Detecting |
| --- | --- |
| 1-propanethiol | Benzene, toluene, ethylbenzene, xylene and chlorinated solvents |
| cysteamine hydrochloride | anions such as nitrate and sulfate |
| 4-(2-pyridylazo)resorcinol modified with a disulfide group | Pb++, Cd++, and Cu++ |
| thiol derivatized dibenzo 18-crown-6 | alkali metals |

The operation of sensor 200 is described with reference to FIG. 2. Integrated optical waveguide sensor 200 includes a SERS structure 10 affixed to an optical assembly 222. Optical assembly 222 includes an optical coupling grating 228 affixed between an optically transparent substrate or element 224 and optical element 226. Optically transparent substrate or element 224, optical element 226, and optical element 14 have indices of refraction $n_1$, $n_2$, and $n_3$ respectively, where $n_2 \rangle n_1$ and $n_2 \rangle n_3$. Materials and properties from which optical elements 224, 226, and 14 may be made are provided, by way of example, in TABLE 2.

TABLE 2

| Item | Material | Index of Refraction |
| --- | --- | --- |
| Optically transparent element 224 | borosilicate glass | $n_1 = 1.51$ |
| Optically transparent element 226 | Corning Glass No. 7059 | $n_2 = 1.56$ |
| Optical element 14 | Silica glass | $n_3 = 1.46$ |

Optical energy source 230 generates an optical excitation signal 232 that is collimated by lens 234 and filtered by filter 236 so as to result in a filtered optical excitation signal 233. Filter 236 filters out all optical signals having wavelengths other than the wavelengths of the optical excitation signal 233. Filtered optical excitation signal 233 is directed through optical structure 222 and into transparent or translucent optical element 14. Coupling gratings 228 helps to couple filtered optical signal 233 into and out of integrated optical waveguide sensor 200. Because the index of refraction $n_2$ of optical element 226 is greater than the indices of refraction of optical substrate 224 ($n_1$) and optical element 14 ($n_2$), optical element 226 serves as a waveguide through which filtered optical signal 233 efficiently propagates. By way of example, optical energy source 230 may be implemented as a Spectra Diode Laser, Inc. Model SDL-5712-H1, for generating optical excitation signal 232 as a monochromatic, coherent light signal having a wavelength of 852 nm.

However, portions of filtered optical signal 233 leak from optical element 226 into optical element 14 and then irradiate samples of an analyte 252 of interest in contact with self-monomer layer 18. Optical signals 233 that come into contact with analyte 252 and self-assembled monolayer 18 undergo a SERS response and are Raman down-shifted in frequency to produce Raman shifted optical signals 237. Portions of Raman shifted optical signals 237 enter and propagate through optical element 14, optical element 226, and optical substrate 224. Some of the Raman shifted optical signals 237 are emitted from integrated optical waveguide sensor 200 and then filtered and transformed by optical filter 240 into filtered Raman shifted optical signals 239. Next, filtered Raman shifted optical signals 239 are focused and directed by optical lens 242 to spectrometer 246, which may for example, be implemented as a Chromex Raman One Spectrometer. Optical filter 240 filters out optical energy at wavelengths equal to or less than the wavelengths of filtered optical signal 233, which may otherwise saturate spectrometer 246. Spectrometer 246 generates an output signal 247 that represents the spectra of Raman emissions that characterize filtered Raman shifted optical, i.e., SERS signals 239. Output signals 247 may then be provided to computer 248 for subsequent processing and analysis.

Figure 7:
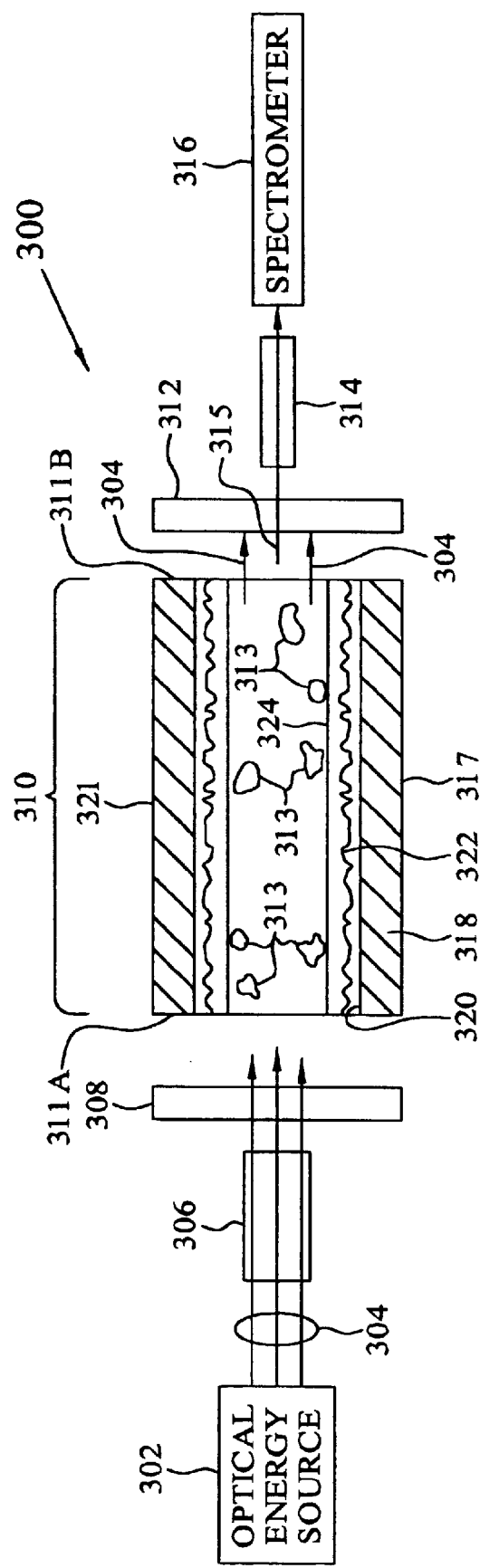
FIG. 7 shows an integrated optical waveguide sensor system that embodies several features of the present invention.

FIG. 7 shows another embodiment of the present invention implemented as integrated optical waveguide sensor system 300 that includes an optical energy source 302 that generates an optical excitation signal 304 that is directed by optical fiber 306 through filter 308 and tubular optical waveguide 310. By way of example, optical energy source 302 may be implemented as a Spectra Diode Laser, Inc. Model SDL-5712-H1, for generating optical excitation signal 304 as a monochromatic, coherent light signal having a wavelength of 852 nm. Filter 308 is an optical bandpass filter that removes emissions due to Raman or fluorescent emissions that may be stimulated in optical fiber 306 by optical excitation signal 304. Optical excitation signal 304 signal enters end 311A of optical waveguide 310. If any analyte of interest 313 is present on the self-assembled monolayer 324 formed around the inside surface of waveguide 313 Raman shifted or SERS light signals 315 and optical excitation signal 304 are emitted from end 311B of tubular waveguide 310. Low pass filter 312 blocks light having wavelengths equal to or shorter than the wavelengths that characterize optical excitation signal 304, but passes Raman shifted optical signal 315 that is directed by optical fiber 314 to spectrometer 316. Optical fibers 306 and 314 preferably are low ⁻OH silica and/or silica clad optical fibers that are transparent to the wavelength of optical excitation signal 304.

Optical waveguide 310 includes a glass tube 318 having a circumferential, inside surface 320 on which a monolithic and textured metal layer 322 is formed. Glass tube 318 may be made of hafnium oxide or other types of glass, having a higher index of refraction than that of distilled water. By way of example, metal layer 322 may be made of gold or silver because these metals are known to provide an excellent SERS response. A self-assembled monolayer 324 is formed over metal layer 322.

Still referring to FIG. 7, in the manufacture of optical waveguide 310, circumferential inside surface 320 of tube 318 is roughened by electrochemical etching to provide surface 320 with, for example, a surface roughness having a maximum peak to valley depth of about 16,000 Å, an average peak to valley depth of about 2,500 Å, and a peak to peak periodicity of about 12.5 microns. Surface 318 may be etched using a chemical etchant such as an HF based cream such as Velvet Etching Cream, manufactured by McKay International. Experience has shown that etching the glass for approximately 1 minute provides the surface roughness characteristics described above. Alternatively, surface 320 may be etched by immersing tube 318 in a dilute solution of 0.1M hydrofluoric acid (HF) for about one minute. Next, metal layer 322 may be formed over roughened inside surface 320 of tube 318 by depositing a monolithic layer 324 of gold or silver over roughened surface 320 using techniques well known by those skilled in the art. After the formation of metal layer 322, tube 318 and more specifically, the inside surface 320, of tube 318 is rinsed with distilled water to remove any salts that may have accumulated on the surface 320. Following the distilled water rinse, tube 318 is rinsed with ethanol ($CH_3CH_2OH$) to remove any distilled water that may be present on the circumferential inside surface 320. Finally, tube 318 is soaked in a dilute solution of thiol for about 24 hours at room temperature to create the self-assembled monolayer 324 on monolithic metal layer 322 inside tube 318.

Another method for manufacturing waveguide 310 is described with reference to FIG. 8. First, tube 318 in a heated or boiling liquid reagent or reagents such as nitric acid, hydrofluoric acid, hydrochloric acid, or potassium hydroxide, for about 30 minutes. Such immersion removes any oils, metallic materials, and other contaminants that may be present on tube 318. Next, substrate tube 318 is removed from the boiling reagent and rinsed in either deionized or distilled water. After the water rinse, tube 318 is immersed in hot or boiling methanol for about 30 minutes, followed by immersion in boiling acetone for about 30 minutes. This procedure removes any organic contaminants that may remain on tube 318. Next, tube 318 is removed from the boiling methanol and allowed to air dry, as for example, about 1 hour. Following cleaning, the process of manufacturing waveguide 310 involves coating the circumferential inside surface 320 of tube 318 with a monolithic, metal coating 340. In order to fabricate metal coating 340, an organic metallic paint that preferably containing a reflective metal such gold or silver, is diluted with toluene or another organic solvent, the concentration of which is not critical, in order to create a diluted paint mixture. Then, the circumferential inside surface 320 of tube 318 is coated with the diluted paint mixture. Next, tube 318 maybe thermally reduced by increasing the temperature of the tube from room temperature up to about 590° C. at a rate of about 5° C./min in a programmable oven such as a Lindberg Model No. 59246-E6. The tube 318 then is heat soaked at 590° C. for about 1 hour, and then allowed to return to room temperature by turning off the oven. The exposure of tube 318 to such temperatures drives off volatile organics, whereby a smooth, reflective metallic coating 320 having a thickness, for example, of about 200 nm is well adhered or affixed to circumferential inside surface 320 of tube 318.

Figure 8:
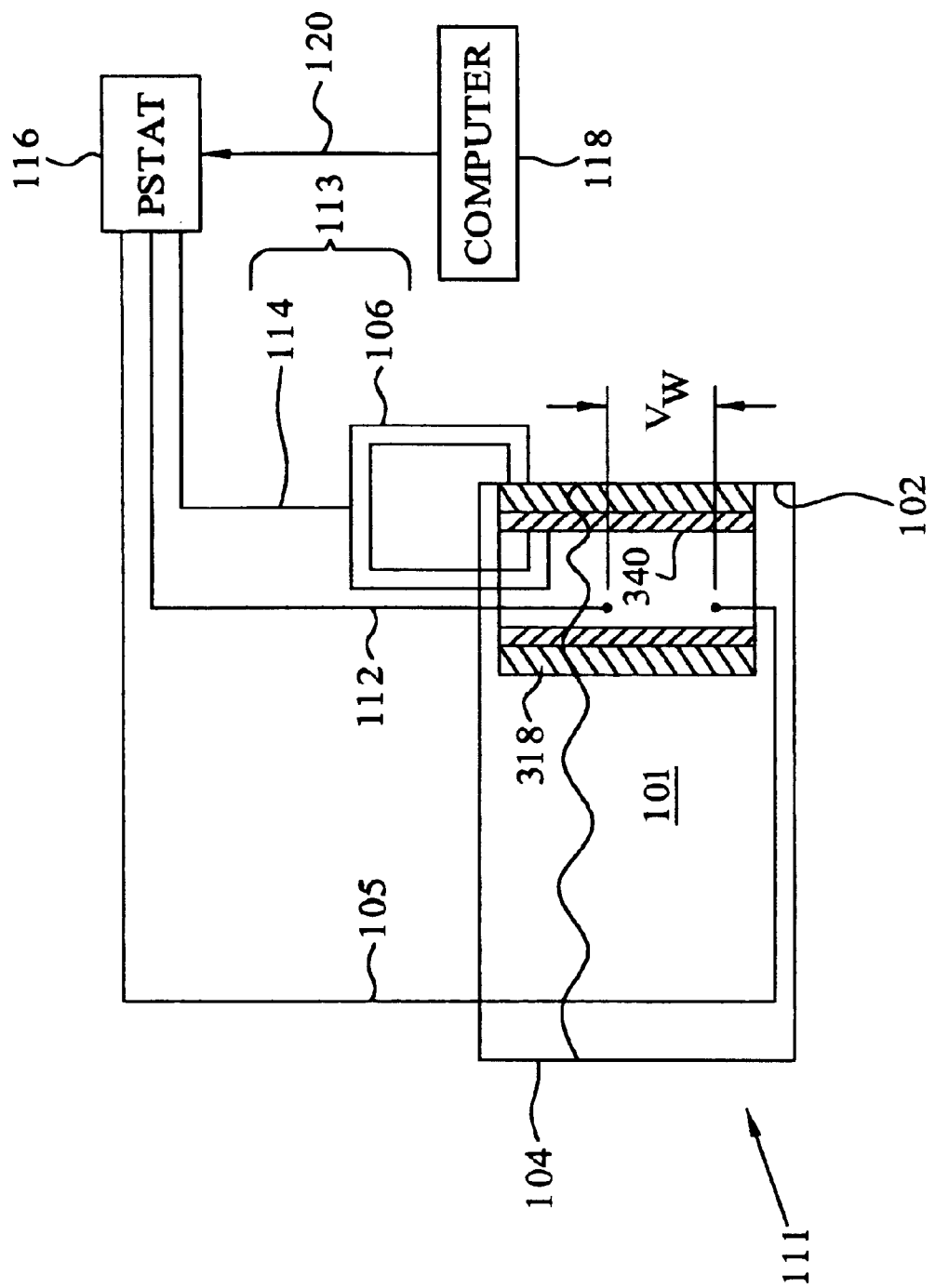
FIG. 8 shows a system for oxidizing and reducing the smooth, reflective metal coating inside the tube of 318.

Next, referring to FIG. 8, tube 318 is subjected to several oxidation/reduction cycles in order to roughen metal coating 340. Tube 318 is immersed in an electrochemical cell 111 that includes electrolyte 101 such as a 0.1M solution of potassium chloride (KCl) held within fluid container 104 and electrodes 105 and 108, and a working electrode 113 comprised of electrical lead 114 and a clamp 106 for holding tube 318 within the electrolyte 101 so that there is electrical continuity between electrode 113 and metal coating 340. It is important that metallic clamp 106 not be immersed in the electrolyte 101 to prevent metallic ions from the clamp from contaminating electrolyte 101. Also immersed in electrolyte 101 are counter electrode 105 and reference electrode 108. Counter electrode 105 preferably is made of platinum wire and is positioned inside the tube 318. Reference electrode 108 preferably is made of silver/silver chloride and is also positioned inside tube 318, but where the tips of electrodes 108 and 105 are separated. Electrodes 105 and 108 are connected to potentiostat 116 as shown. Similarly, clamp 106 is connected via wire 114 to potentiostat 1116. Potentiostat 116 maintains appropriate voltage levels at each of electrodes 105 and 108, and electrode 113 under the supervision of computer 118 via signal line 120.

Figure 9:
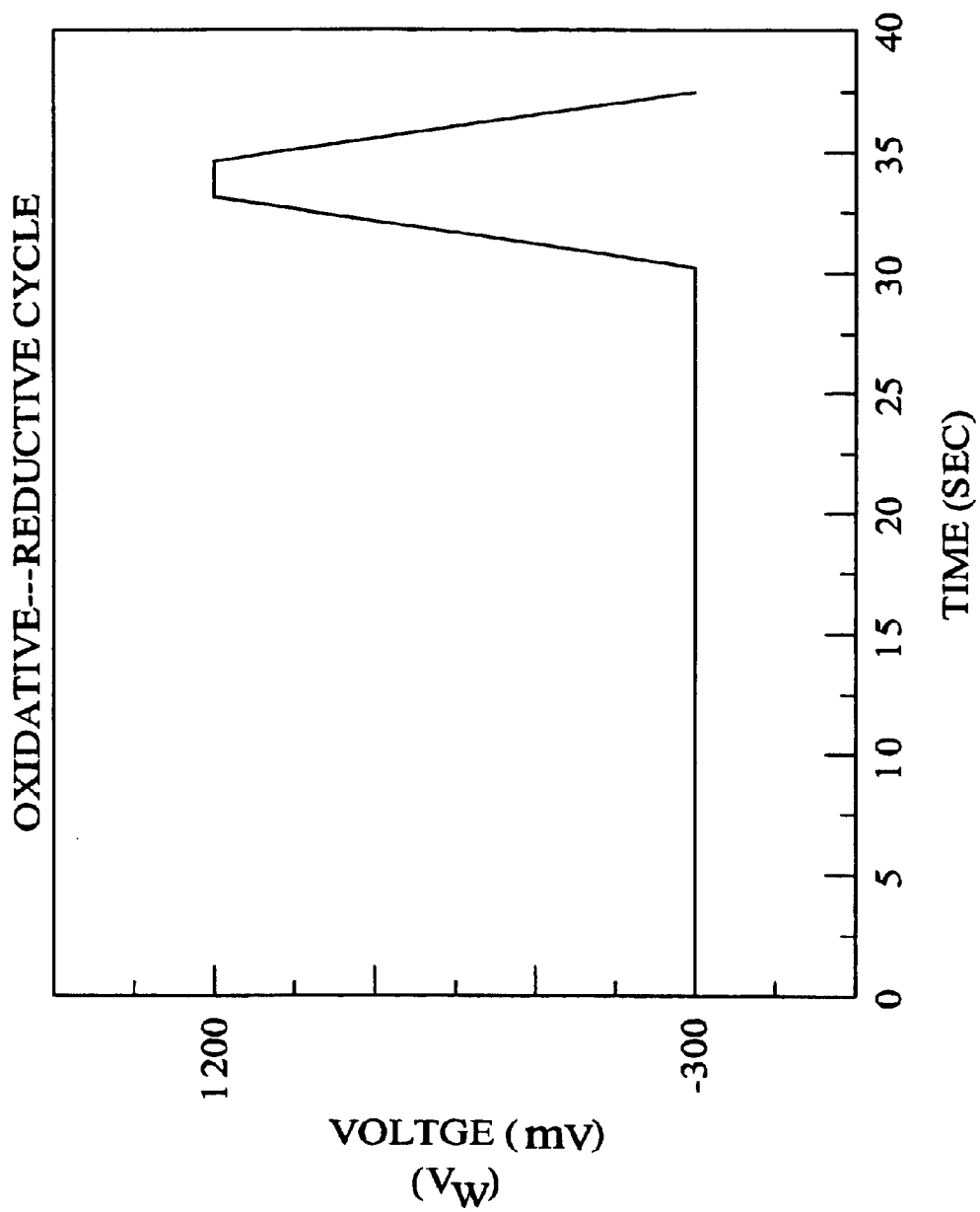
FIG. 9 is a graph representing one period of an oxidation-reduction cycle used to manufacture a SERS structure in the electrochemical cell of FIG. 7.

Still referring to FIG. 8, voltage, $V_W$, of working electrode 113 is modulated from −300 mV to 1200 mV with respect to the voltage of reference electrode 108 for a predetermined number of oxidative-reductive cycles, as required to suit the needs of a particular application. An example of an oxidative-reductive cycle is shown, by way of example, in FIG. 9. In an oxidative-reductive cycle, $V_W$ is held at −300 mV for about 30 seconds and then ramped to 1200 mV at a rate of about 500 mV/s. Next, $V_W$ is held at 1200 mV for about 1.3 seconds and then reduced to −300 mV at a rate of about −500 mV/s. Subjecting metal coating 340 to preferably 25 oxidative-reductive cycles of the type described above transforms smooth, monolithic metal coating 340 into a roughened metal coating 340 having an average surface roughness of about 20 Å, thereby creating a patterned metal SERS structure.

After creating roughened metal coating 340, tube 318 is rinsed with distilled water to remove any salts that may have accumulated on the surfaces of tube 318 and roughened metal layer 340. Following the distilled water rinse, tube 318 is rinsed with ethanol ($CH_3CH_2OH$) to remove any distilled water that may be present on surfaces of tube 318 and roughened metal layer 340. Finally, tube 318 is soaked in a dilute solution of thiol for about 24 hours at room temperature to create the self-assembled monolayer 324 on monolithic metal layer 322 inside tube 318, and thereby create waveguide 310.

Obviously, many modifications and variations of the present invention are possible in light of the above teachings. It is therefore to be understood that within the scope of the appended claims, the invention may be practiced otherwise than as specifically described.

What is claimed is:

1. An integrated optical waveguide sensor system, comprising:
    an optical waveguide having a monolithic and roughened metallic layer on which a self-assembled monolayer is formed, wherein said optical waveguide comprises:
      a first optical element having a first index of refraction $n_1$;
    a second optical element affixed to said first optical element and having a second index of refraction $n_2$, where $n_2 > n_1$;
      an optical coupling grating affixed between said first and second optical elements; and
      a third optical element affixed to said second optical element and having a third index of refraction $n_3$, where $n_2 > n_3$, and wherein said third optical element has a roughened surface and includes an adhesion layer formed on said roughened surface;
    an optical energy source for generating an optical excitation signal; and
    a spectrometer for detecting spectra of optical energy emitted from said optical waveguide.

2. The integrated optical waveguide sensor system of claim 1 wherein said optical waveguide is shaped as a tube.

3. The integrated optical waveguide sensor system of claim 2 further including a first optical fiber for directing said optical excitation signal into said optical waveguide.

4. The integrated optical waveguide sensor system of claim 2 further including a second optical fiber for directing said spectra of optical energy emitted from said optical waveguide to said spectrometer.

5. The integrated optical waveguide sensor system of claim 1 which further includes a first optical bandpass filter.

6. The integrated optical waveguide sensor system of claim 1 which further includes a second optical bandpass filter interposed between said optical waveguide and said spectrometer for substantially preventing said optical excitation signal from irradiating said spectrometer.

7. The integrated optical waveguide sensor system of claim 1 wherein said roughened metallic layer is formed on a roughened surface of a glass substrate.

8. The integrated optical waveguide sensor system of claim 1 wherein said metal layer consists essentially of a metal selected from the group that includes copper, silver, and gold.

9. The integrated optical waveguide sensor system of claim 8 wherein said metal layer is formed by vapor depositing said metal layer on said adhesion layer.

10. The integrated optical waveguide sensor system of claim 1 wherein said self-assembled monolayer is made from a thiol selected from the group that includes 1-propanethiol, cysteamine hydrochloride, 4-(2-pyridylazo) resorcinol modified with a disulfide, and thiol derivatized debenzo 18-crown-6.

11. The integrated optical waveguide sensor system of claim 1 wherein said roughened surface has an average surface roughness that does not exceed about 2,500 Å and an average peak to peak periodicity that does not exceed about 12.5 microns.

12. The integrated optical waveguide sensor system of claim 1 wherein said roughened surface has an average peak to peak periodicity that does not exceed about 12.5 microns.

13. The integrated optical waveguide sensor system of claim 1 wherein said second optical element is made of glass, and $n_2 \approx 1.56$.

14. The integrated optical waveguide sensor system of claim 1 wherein said first optical element consists essentially of borosilicate, and $n_1 \approx 1.51$.

15. The integrated optical waveguide sensor system of claim 1 wherein said third optical element is made of silica glass, and $n_3 \approx 1.46$.

* * * * *